United States Patent [19]

Christensen et al.

[11] Patent Number: 4,650,794
[45] Date of Patent: Mar. 17, 1987

[54] 6-(1-HYDROXYETHYL)-2-CARBAMIMID-OYL-PEN-2-EM-3-CARBOXYLIC ACIDS

[75] Inventors: Burton G. Christensen, Cliffside Park; Frank P. DiNinno, Old Bridge; William J. Leanza, Berkeley Heights; Ronald W. Ratcliffe, Matawan, all of N.J.

[73] Assignee: Merck & Co., Inc., Rahway, N.J.

[21] Appl. No.: 373,088

[22] Filed: Apr. 29, 1982

[51] Int. Cl.$^4$ .................. C07D 499/00; A61K 31/425
[52] U.S. Cl. ...................................... 514/210; 540/310; 544/333; 546/272
[58] Field of Search ...................... 260/245.2 R, 239.1; 424/270, 271; 540/310; 514/210; 544/333; 546/272

[56] References Cited

U.S. PATENT DOCUMENTS 4,395,418  7/1983  Ohki et al. .................. 260/245.2 R
4,517,124  5/1985  Broom ........................ 260/245.2 R

FOREIGN PATENT DOCUMENTS 0046363  2/1982  European Pat. Off. .

OTHER PUBLICATIONS

Tetrahedron Letters, vol. 23, No. 8, pp. 897–900 (1982).

Primary Examiner—Nicholas S. Rizzo
Attorney, Agent, or Firm—Raymond M. Speer; Hesna J. Pfeiffer

[57] ABSTRACT

Disclosed are 6-(1-hydroxyethyl)-2-carbamimidoyl-pen-2-em-3-carboxylic acids (I) having the representative structure:

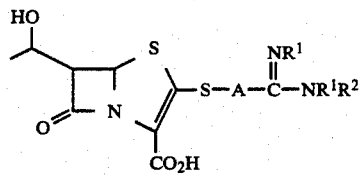

wherein: A is a direct, single bond connecting the indicated S and C atoms, or A is a cyclic or acyclic connecting group selected, inter alia, from alkyl, cycloalkyl, aryl, heteroaryl, heteroalkyl; $R^1$ and $R^2$, which define the carbamimidoyl function, are, inter alia, independently selected from hydrogen, alkyl, aryl, alkoxy, amino; additionally, said carbamimidoyl is characterized by cyclic structures achieved by the joinder of the two nitrogen atoms via their substituents and by their joinder to connecting group A; additionally, "carbamimidiums" are disclosed by quaternization of one of the nitrogen atoms of said carbamimidoyl. Such compounds as well as their pharmaceutically acceptable salt, ester and amide derivatives are useful as antibiotics. Also disclosed are processes for the preparation of such compounds; pharmaceutical compositions comprising such compounds; and methods of treatment comprising administering such compounds and compositions when an antibiotic effect is indicated.

4 Claims, No Drawings

6-(1-HYDROXYETHYL)-2-CARBAMIMIDOYL-PEN-2-EM-3-CARBOXYLIC ACIDS

BACKGROUND OF THE INVENTION

This invention relates to 6-(1-hydroxyethyl-2-carbamimidoyl-pen-2-em-3-carboxylic acids (I) and the pharmaceutically acceptable salt, ester and amide derivatives thereof which are useful as antibiotics:

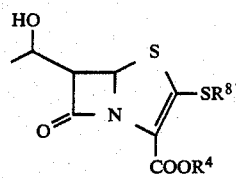

wherein: $R^8$ is generically defined to be a "carbamimidoyl", which may be defined by the following structures:

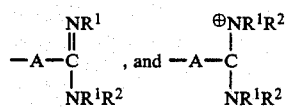

wherein A, the cyclic or acylic connecting group, and $R^1$ and $R^2$ are defined below. The definition of $R^8$ also embraces cyclic structures, which may be generically represented, for example, thusly:

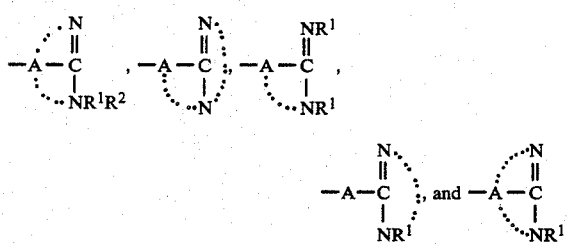

wherein the dotted lines indicate that the nitrogen atoms of the so-called carbamimidoyl function may participate in the formation of the cyclic structures indicated above. Representative specific embodiments for $R^8$ follow, but, in the generic sense, the components: $R^1$, $R^2$ and A which comprise $R^8$ are defined, thusly:

A, the cyclic or acyclic connector, is selected from the group consisting of alkyl, alkenyl, and alkynyl having 1-10 carbon atoms which may be interrupted by a hetero atom selected from O, S or N, or by a ring such as phenyl, cycloalkyl, cycloalkenyl, heterocyclyl or heteroaryl wherein such cyclic interruptions comprise 3-6 ring atoms selected from C, O, S and N; cycloalkyl, cycloalkenyl having 3-6 carbon atoms; heterocyclyl; heteroaryl; and phenyl; A also represents a direct, single bond connecting the indicated S and C atoms.

$R^1$ and $R^2$ are independently selected from hydrogen, alkoxyl, amino, mono- and disubstituted amino, and the previously defined values for the group A, such as: alkyl, aryl, cycloalkyl, heteroalkyl, alkylaryl, alkylarylalkyl, and heterocyclyl and heteroaryl.

$R^4$ is hydrogen, a removable protecting group, a synthetically useful salt moiety, or a pharmaceutically acceptable salt or ester moiety.

It should be noted that the final products of this invention (I) can exist in either neutral or zwitterionic (internal salt) forms. In the zwitterionic form, the basic function is protonated and positively charged and the carboxyl group is deprotonated and negatively charged. The zwitterionic form is the predominant species under most conditions and is in equilibrium with a minor amount of the uncharged, neutral species. The equilibrium process is conveniently visualized as an internal acid-base neutralization. The neutral and zwitterionic forms are shown below.

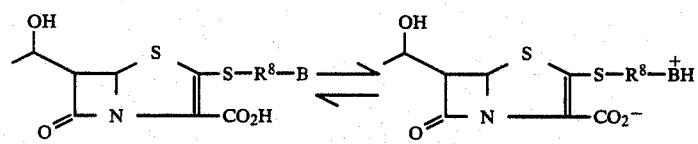

wherein B is the carbamimidoyl group.

Further, the final products of this invention I wherein $R^8$ contains a positively charged quaternary nitrogen function such as the "carbamimidinium" can exist as zwitterionic (internal salt) forms or as external salt forms. The preferred form of this product group is the zwitterionic or internal salt form. These forms are shown below:

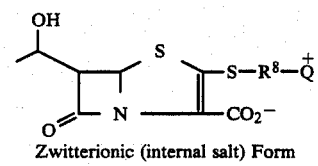

Zwitterionic (internal salt) Form

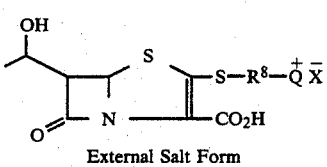

External Salt Form wherein Q represents the quaterized nitrogen group, and wherein X is a pharmaceutically acceptable anion such as those listed in U.S. Pat. No. 4,194,047, issued 3/18/80, which is incorporated herein by reference.

This invention also relates to the carboxyl derivatives of I which are antibiotics and which may be represented by the following generic structure (I):

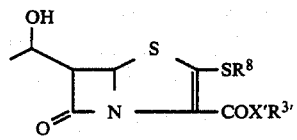

wherein X' is oxygen, sulphur or NR' (R'=H or lower alkyl having 1-6 carbon atoms; and $R^{3'}$ is, hydrogen, or, inter alia is representatively selected to provide the pharmaceutically acceptable salt, ester, anhydride ($R^{3'}$ is acyl), and amide moieties known in bicyclic β-lactam antibiotic art; $R^{3'}$ may also be a readily removable blocking group. The definition of $R^{3'}$ is given in greater detail below.

This invention also relates to processes for the preparation of such compounds I; pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inaminate systems. These antibiotics are active against a broad range of pathogens which representatively include both Gram positive bacteria such as *S. aureus, Strep. pyogenes,* and *B. subtilis,* and Gram negative bacteria such as *E. coli,* Pseudomonas, *Proteus morganii,* Serratia, and Klebsiella. Further objects of this invention are to provide chemical processes for the preparation of such antibiotics and their nontoxic, pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

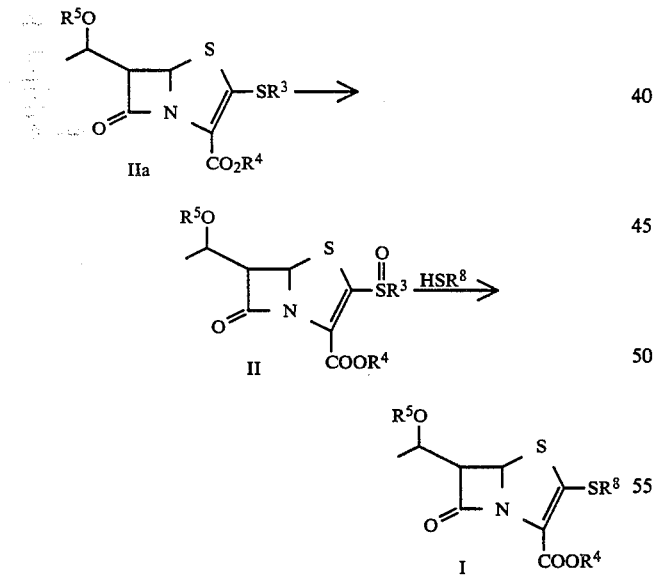

Transformation IIa to II.

Relative to the above reaction scheme, there is no undue criticality as to the precise identity of the oxidizing agent. Suitable oxidizing agents include peracids such as m-chloroperbenzoic acid and peracetic acid. Other representative oxidizing agents include potassium permanganate, hydrogen peroxide, sodium meta periodate, t-butyl hydrogen peroxide, dichloroiodobenzene, sulfuryl chloride with wet silica gel, sodium hypochlorite, and ozone, for example. Typically, 1.0 eq. to a slight excess of oxidizing reagent is employed. There is no criticality as to reaction solvent—any solvent being acceptable which is inert or substantially inert during the course of reaction and which effectively solubilizes the starting material IIa. Representative examples of suitable solvents for the oxidation include tetrahydrofuran, methylenechloride, dimethylformamide, methanol and water. Typically, the reaction is conducted at a temperature of from about $-78°$ to $50°$ C., for from a few minutes to several hours. As mentioned above, starting materials IIa are known.

Transformation II to I

The transformation II to I is accomplished by treating II with the reagent of choice, $HSR^8$, in the presence of a base. Suitable bases for this reaction include N-heterocycles, amines, trialkylamines, and inorganic bases, such as, diisopropylethylamine, triethylamine, N-methylpiperidine, potassium carbonate, and sodium bicarbonate. In the alternative, the reaction may proceed without the addition of base when the $HSR^8$ reagent is taken as its salt: $M^{+-}SR^8$ wherein $M^+$ is $Li^+$, $Na^+$, $K^+$ or $R_4N^+$, for example: wherein R is independently chosen from: alkyl having 1–16 carbon atoms or aralkyl having 7–12 carbon atoms; for example: methyl, ethyl, butyl, benzyl, hexadecyl or the like. Typically, the reaction is run in a solvent such as dimethylformamide, acetonitrile, dimethylsulfoxide, water or mixtures thereof, at a temperature of from $-50°$ to $30°$ C. (preferably in the range from $-30°$ to $15°$ C.) for from 1 min to 24 hours. Reactions are conducted in water as the solvent or cosolvent can be kept in the pH 7–8.5 range with a suitable buffer.

Preferably, the reaction II to I is conducted in the presence of a sulfenic acid trap. The sulfenic acid trap may be accomplished by using excess $HSR^8$ or, in the alternative, using relatively, non-reactive, mercaptans such as trityl mercaptan, olefins such as: cyclohexene, isobutylene, dihydropyran; phosphines such as triphenyl phosphine, tributylphosphine, or the like, may also be employed.

Relative to starting material II, commonly assigned U.S. patent application Ser. Nos. 353,451 (filed 3/1/82) is incorporated herein by reference to the extent that it defines II and its manner of preparation:

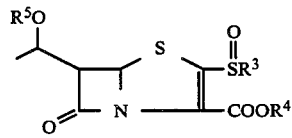

In brief, relative to starting material II, $R^3$ is alkyl, aralkyl, or cycloalkyl and $R^5$ is hydrogen or a hydroxyl protecting group; such hydroxyl protecting groups include: triorganosilyl wherein the organo moiety is independently selected from alkyl having 1–6 carbon atoms, phenyl, and phenylalkyl, for example, t-butyldimethylsilyl; $PNBO_2C$, $TCEO_2C$, and the like. They are prepared from the corresponding 2-$SR^3$ species (IIa) by oxidation. The 2-$SR^3$ starting penems are known. See U.S. Pat. No. 4,260,618 (issued 4-7-81); U.K. patent application G.B. No. 201 3674 A (published 15 Aug. 1979); and U.K. patent application G.B. No. 2042520H (published 24 Sept. 1980), which documents are incorporated herein by reference. [PNB=p-nitrobenzyl; TCE=2,2,2-trichloroethyl.]

HSR[8] Reagents

Relative to the foregoing description of the invention, suitable carbamimidoyl and carbamimidinium mercaptans HSR[8] which are utilized in the transformation II to I are listed below. Wherein R[8] is:

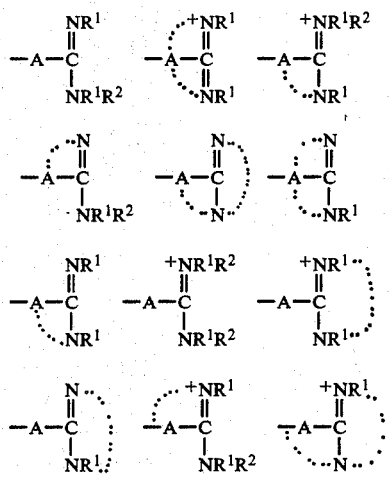

and wherein $R^1$ and $R^2$ are as initially defined under $R^8$; the two nitrogen atoms demonstrated in the above structure may participate in cyclic structures which are indicated by the dotted lines; A is a connecting group between the sulfur atom and carbamimidoyl function. It should be noted that while not all conical forms of $R^8$ are reproduced herein, the foregoing list is representative and constitutes together with the associated text a definition of the "carbamimidoyl" group of the present invention.

$R^1$ and $R^2$ are independently selected from the group consisting of hydrogen, amino, mono- and disubstituted amino (wherein the substituent is alkyl having 1–6 carbon atoms), alkoxyl (having 1–6 carbon atoms); substituted and unsubstituted: straight and branched alkyl having from 1 to 6 carbon atoms; cycloalkyl having 3 to 6 carbon atoms; cycloalkylalkyl wherein the cycloalkyl moiety comprises 3 to 6 carbon atoms and the alkyl moiety comprises 1 to 6 carbon atoms; alkylcycloalkyl wherein the alkyl moiety comprises 1 to 6 carbon atoms and the cycloalkyl moiety comprises 3 to 6 carbon atoms; aryl such as phenyl; arylalkyl such as benzyl; heterocyclyl (saturated and unsaturated) comprising mono- and bicyclic structures having from 5 to 10 ring atoms, wherein one or more of the heteroatoms is selected from oxygen, nitrogen, or sulfur, such as thiophene, imidazole, tetrazolyl, furyl, pyridine; heterocyclylalkyl groups which comprise the immediately preceding heterocyclyl moieties and the alkyl moiety comprises 1 to 6 carbon atoms. The substituent or substituents relative to the above-named radicals comprising $R^1$ and $R^2$ are selected from the group consisting of amino, hydroxy, cyano, carboxyl, nitro, chloro, bromo, fluoro, alkoxy, and alkylthio having from 1 to 6 carbon atoms, mercapto, perhaloalkyl having 1 to 3 carbon atoms, guanidino, amidino, sulfamoyl. When located on the same nitrogen atom, the substituents $R^1$ and $R^2$ can be joined to form a cyclic group comprising 3–8 atoms. The resulting ring can contain additional O, S or N atoms. For example, $-NR^1R^2$ can be taken as morpholino, pyrrolidino, piperidino, azetidinyl or the like.

Particularly preferred groups under the definition of $R^1/R^2$ are: hydrogen; substituted and unsubstituted: straight and branched loweralkyl having from 1 to 6 carbon atoms; cycloalkyl having from 3 to 6 carbon atoms, cycloalkylalkyl wherein the cycloalkyl moiety comprises 3 to 6 carbon atoms and the alkyl moiety comprises 1 to 6 carbon atoms; aryl such as phenyl, arylalkyl such as benzyl; the substituents on the above-named radicals are selected from fluoro, hydroxy, mercapto, amino, alkoxy and alkylthio having from 1 to 3 carbon atoms.

In defining the bivalent, cyclic or acyclic connector group "A", it is to be noted that the recited radicals of definition are to be read both left to right and right to left. Thus, the preferred connecting groups "A" are selected from: substituted and unsubstituted: loweralkyl having from 1–6 carbon atoms; cycloalkyl having from 3–10 atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; loweralkenyl having from 2–10 carbon atoms, cycloalkenyl having from 3 to 10 carbon atoms, cycloalkenylalkyl wherein the cycloalkenyl moiety comprises 3 to 10 carbon atoms; and the alkyl moiety comprises 1 to 6 carbon atoms; alkynyl having from 2 to 10 carbon atoms; aryl such as phenyl and naphthyl; arylalkyl and alkylaryl such as benzyl, phenethyl and the like; heteroalkyl, alkylheteroalkyl, arylheteroarlky and alkylheteroaryl wherein the hetero atoms are selected from the group of sulfur, oxygen and nitrogen, and the alkyl moiety has 1 to 6 carbon atoms, and the aryl moiety is phenyl; heterocyclyl (saturated and unsaturated) comprising mono- and bicyclic structures having 5 to 10 ring atoms wherein one or more of the hetero atoms is selected from oxygen, nitrogen, or sulphur such as thiophene, imidazole, pyridine, furyl and the like; heterocyclyalkyl wherein the heterocyclyl moiety comprises from 3 to 10 atoms and the alkyl moiety comprises from 1 to 6 atoms; the substituent (or substituents) relative to the above-named radicals are selected from the group consisting of amino, hydroxyl, cyano, carboxyl, nitro, chloro, bromo, fluoro, alkoxy having from 1 to 6 carbon atoms, mercapto, perhaloloweralkyl such as trifluoromethyl and alkylthio having from 1–6 carbon atoms.

A particularly preferred class of connecting groups "A" are selected from: a single bond connecting the sulfur and carbamimidoyl function; substituted and unsubstituted: straight and branched loweralkyl having from 1 to 6 carbon atoms, cycloalkyl having from 3 to 6 carbon atoms; phenyl; heterocyclyl such as thiophene, imidazole, pyridine, and furan; alkylheteroalkyl wherein alkyl moiety comprises 1 to 3 carbon atoms and the hetero atoms are sulfur, oxygen and nitrogen; the substituents relative to the above-named radicals are: amino, hydroxyl, chloro, bromo, fluoro, cyano, carboxyl alkoxy having from 1 to 3 carbon atoms, mercapto, trifluoromethyl, and alkylthio having from 1 to 3 carbon atoms.

Representative examples of such preferred $-SR^8$ groups (represented as HSR[8]) are:

EXAMPLES

- $HS-CH_2-\underset{\substack{\| \\ NH}}{C}-NH_2$
- $HS-CH_2-\underset{\substack{\| \\ NH}}{C}-NHCH_3$
- $HS-CH_2-\underset{\substack{\| \\ NH}}{C}-NH(CH_3)_2$
- $HS-CH_2-\underset{\substack{\| \\ NCH_3}}{C}-NHCH_3$
- $HS-CH_2-\underset{\substack{\| \\ N-C_2H_5}}{C}-NH_2$
- $HS-CH_2-\underset{\substack{\| \\ NH}}{C}-\underset{\substack{| \\ C_2H_5}}{N}CH_3$
- $HS-CH_2-\underset{\substack{\| \\ NH}}{C}-N(C_2H_5)_2$
- $HS-CH_2-\underset{\substack{\| \\ NH}}{C}-\underset{\substack{| \\ H}}{N}C-(CH_3)_3$
- $HS-\underset{\substack{| \\ CH_3}}{CH}-\underset{\substack{\| \\ NH}}{C}-NH_2$
- $HS-\underset{\substack{| \\ CH_3}}{CH}-\underset{\substack{\| \\ NH}}{C}-NHCH_3$
- $HSCH_2-\underset{\substack{\| \\ NCH_3}}{C}-N(CH_3)_2$
- $HS-\underset{\substack{| \\ CH_3}}{CH}-\underset{\substack{\| \\ NH}}{C}-N(CH_3)_2$
- $HS-\underset{\substack{| \\ \phi}}{CH}-\underset{\substack{\| \\ NH}}{C}-NH_2$
- $HS-\underset{\substack{| \\ CH_2}}{C}-\underset{\substack{\| \\ NH}}{C}-NH_2$
- $HS-\underset{\substack{| \\ CH=CH_2}}{CH}-\underset{\substack{\| \\ NH}}{C}-NH_2$
- $HS-CH_2-CH_2-\underset{\substack{\| \\ NH}}{C}-NH_2$
- $HS-CH_2-\underset{\substack{| \\ OCH_3}}{CH}-\underset{\substack{\| \\ NH}}{C}-NH_2$
- $HSCH_2-\underset{\substack{| \\ OH}}{CH}-\underset{\substack{\| \\ NH}}{C}-NH_2$
- $HS-CH_2-\underset{\substack{| \\ N-OCH_3}}{CH}-\underset{\substack{\| \\ NH}}{C}-NH_2$
- $HS-CH_2-\underset{\substack{| \\ N(CH_3)_2}}{CH}-\underset{\substack{\| \\ NH}}{C}-NH_2$
- $HSCH-\underset{\substack{| \\ CO_2H}}{\phantom{C}}-\underset{\substack{\| \\ NH}}{C}-N(CH_3)_2$
- $HS-CH_2-\underset{\substack{| \\ S \\ | \\ CH_3}}{CH}-\underset{\substack{\| \\ NH_2}}{C}=NH$
- $HSCH_2-\underset{\substack{\| \\ NH}}{C}-NH\phi$
- $HS(CH_2)_n-\underset{\substack{\| \\ NR^2}}{C}-NHR^1$
  n = 2-5, $R^2$ = H, $CH_3$
  $R^1$ = H, $CH_3$
- $HS(CH_2)_n\underset{\substack{| \\ CH_3}}{\overset{\substack{CH_3 \\ |}}{C}}-\underset{\substack{\| \\ NH_2}}{C}=NH$
- $HS-(CH_2)_n-\underset{\substack{\| \\ NR^2}}{C}-NR^1R^2$
  n = 2-5, $R^1$, $R^2$ = H, $CH_3$
- $HS-(CH_2)_2-S-CH_2-\underset{\substack{\| \\ NH}}{C}-N(CH_3)_2$
- $HS-(CH_2)_2-O-CH_2CH_2-\underset{\substack{\| \\ NH}}{C}-NH_2$
- $HS-\underset{\substack{| \\ CH_3}}{\overset{\substack{CH_3 \\ |}}{C}}-\underset{\substack{\| \\ NH_2}}{C}=NH$
- $HS-\underset{\substack{| \\ CH_3}}{\overset{\substack{CH_3 \\ |}}{C}}-CH_2-\underset{\substack{\| \\ NH_2}}{C}=NH$
- $HS-\underset{CH_3}{CH}-CH_2-S-\underset{\substack{\| \\ NH}}{C}-N(CH_3)_2$
- $HSCH=CH-\underset{\substack{\| \\ NH}}{C}-N(CH_3)_2$ -continued
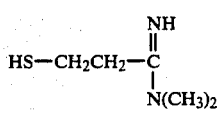
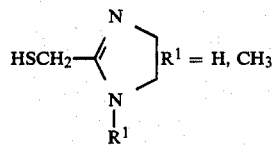 R¹ = H, CH₃
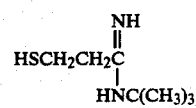
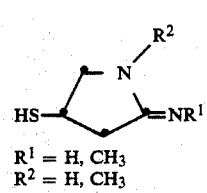
R¹ = H, CH₃
R² = H, CH₃
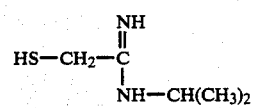
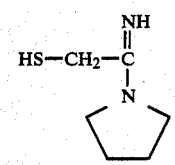
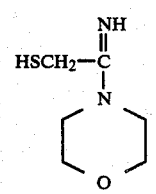
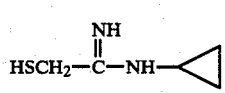
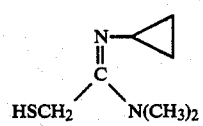
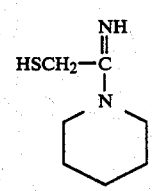
-continued
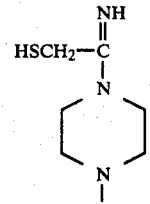
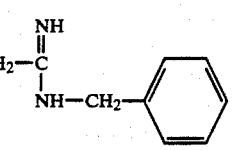
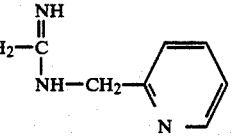
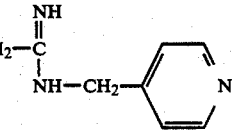
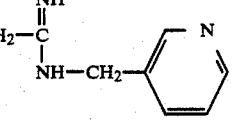
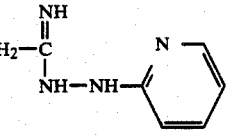
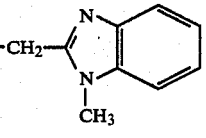
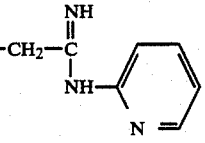
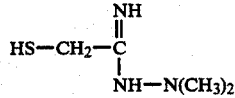
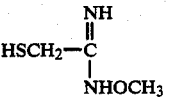
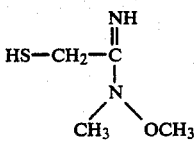

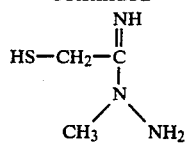
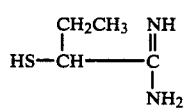
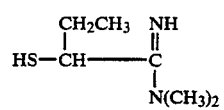
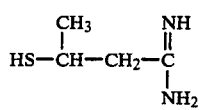
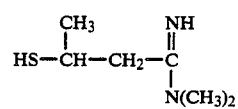
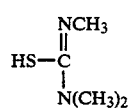
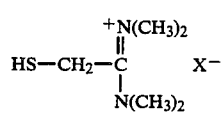
X = any compatible anion
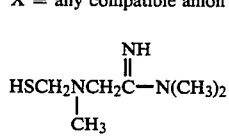
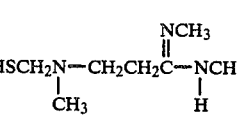
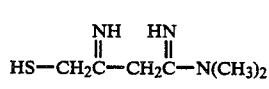
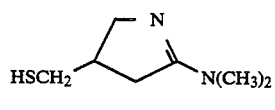
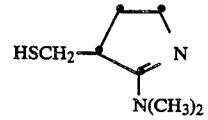
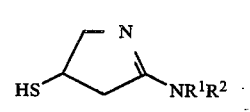
$R^1$ = H, $CH_3$
$R^2$ = H, $CH_3$
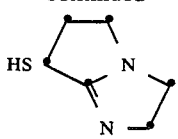
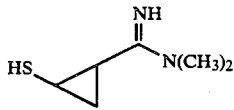
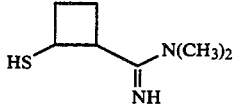
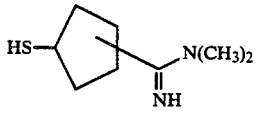
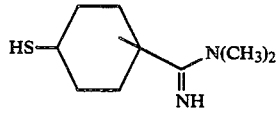
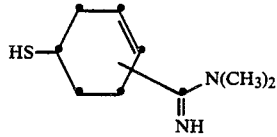
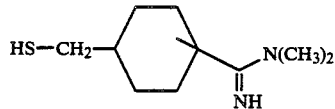
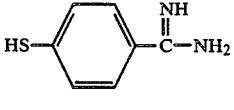
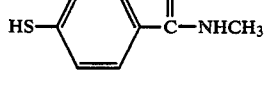
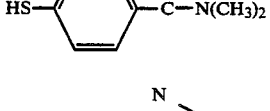
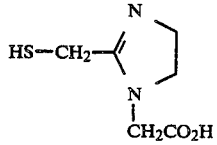
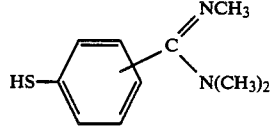

-continued
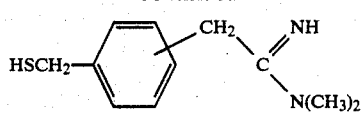
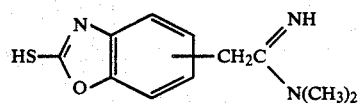
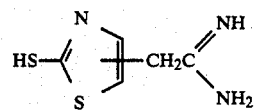
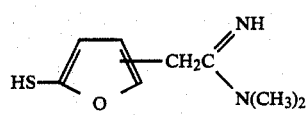
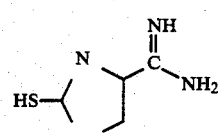
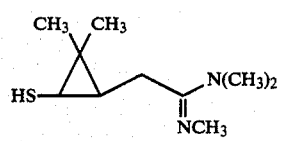
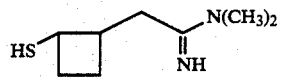
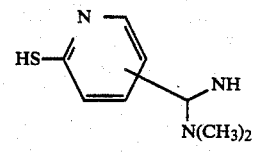
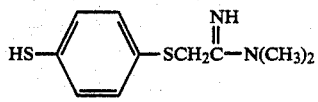
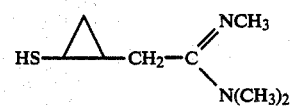
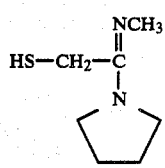
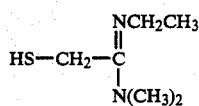
-continued
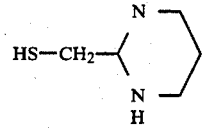
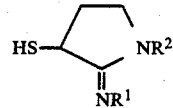
$R^1$ = H, CH$_3$
$R^2$ = H, CH$_3$
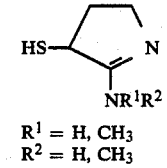
$R^1$ = H, CH$_3$
$R^2$ = H, CH$_3$
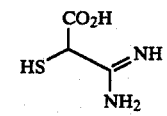
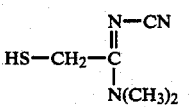
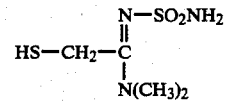
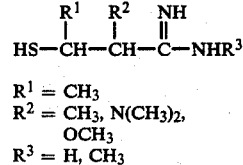
$R^1$ = CH$_3$
$R^2$ = CH$_3$, N(CH$_3$)$_2$, OCH$_3$
$R^3$ = H, CH$_3$
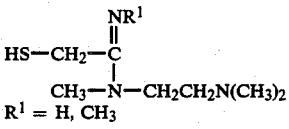
$R^1$ = H, CH$_3$
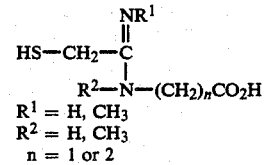
$R^1$ = H, CH$_3$
$R^2$ = H, CH$_3$
n = 1 or 2
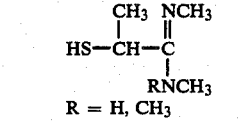
R = H, CH$_3$
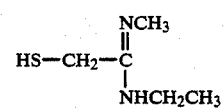

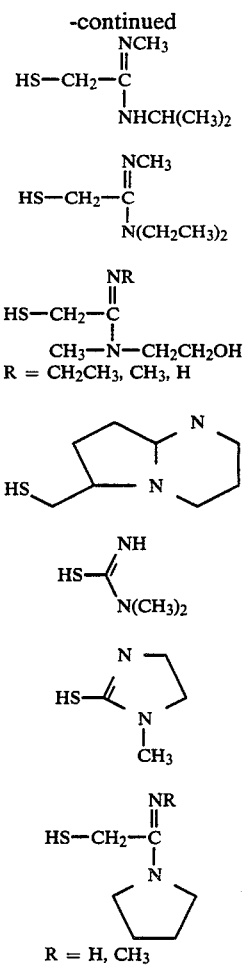

R = CH₂CH₃, CH₃, H

R = H, CH₃

It is recognized that SR⁸ side chains in which the R⁸ group contains one or more chiral centers can be added as racemic or diastereomeric mixtures to provide mixtures of diastereomeric products or can be added as resolved, isomerically pure reagents to provide diastereomerically pure products. Since antibacterial activity and other pharmacological properties vary among isomers, it is frequently advantageous to prepare isomerically pure products by the introduction of resolved —SR⁸ side chains.

As noted above, the compounds of the present invention may also generally be represented by the following structural formula:

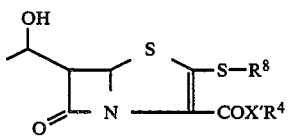

wherein X' is oxygen, sulfur or NR' (R' is hydrogen or loweralkyl having from 1 to 6 carbon atoms); and R⁴ is hydrogen, or, inter alia, is representatively selected to provide the pharmaceutically acceptable salt, ester, anhydride (R⁴ is acyl), and amide moieties known in the bicyclic β-lactam antibiotic art; R⁴ may also be a readily removable blocking group or a synthetic useful salt moiety. A synthetically useful salt moiety consists of a highly lipophilic carboxylate cation which imparts organic solubility to the molecule. This type of carboxylate derivative allows reactions, and particularly the displacement reaction of II to I, to be conducted in an organic solvent. Representative examples of such highly lipophilic carboxylate cations R⁴ are ammonium salts R₄ᵃN⁺ wherein Rᵃ are independently selected from 1–16 carbon alkyl groups or 7 to 10 carbon aralkyl groups. A particularly useful example of this type is the N,N-dimethyl-N-benzyl-N-hexadecyl ammonium salt.

Identification of the Radical —COX'R⁴

In the generic representation of the compounds of the present invention (I, above), the radical represented by —COX'R⁴ is, inter alia, —COOH (X' is oxygen and R⁴ is hydrogen) and all radicals known to be effective as pharmaceutically acceptable ester, anhydride (R⁴ is acyl) and amide radicals in the bicyclic β-lactam antibiotic art, such as the cephalosporins and penicillins and nuclear analogues thereof.

Suitable, but representative, blocking esters R⁴ (X'=O) include those selected from the following list which is representative:

(i) R⁴=CRᵃRᵇRᶜ wherein at least one of Rᵃ, Rᵇ, and Rᶜ is an electron-donor, e.g., p-methoxyphenyl. The remaining Rᵃ, Rᵇ and Rᶜ groups may be hydrogen or organic substituting groups. Suitable ester groups of this type include p-methoxybenzyloxycarbonyl.

(ii) R⁴=CRᵃRᵇRᶜ wherein at least one of Rᵃ, Rᵇ and Rᶜ is an electron-attracting group, e.g., p-nitrophenyl, trichloromethyl, and o-nitrophenyl. Suitable esters of this type include p-nitrobenzyloxycarbonyl, 2,2,2-trichloroethoxycarbonyl, and acetonyloxycarbonyl.

(iii) R⁴=CRᵃRᵇRᶜ wherein at least two of Rᵃ, Rᵇ and Rᶜ are hydrocarbon such as alkyl, e.g., methyl or ethyl, or aryl, e.g., phenyl and the remaining Rᵃ, Rᵇ and Rᶜ group, if there is one, is hydrogen. Suitable esters of this type include t-butyloxycarbonyl, diphenylmethoxycarbonyl, triphenylmethoxycarbonyl, and allyloxycarbonyl.

Silyl esters. This category of blocking groups, may conveniently be prepared from a halosilane of the formula: R₃⁴°SiX° wherein X° is a halogen such as chloro or bromo and R⁴° is independently chosen from: alkyl, having 1–6 carbon atoms, phenyl, or phenylalkyl. Suitable esters of this type include t-butyldiphenylsilylcarbonyl.

Pharmaceutically acceptable carboxyl derivatives of the present invention are those derived by reacting I with alcohols, acylating reagents and the like. For example, esters and amides of interest are the above-listed starting materials and final products having the —COX'R⁴ group at the 3-position; wherein X' is oxygen, sulfur or NR' (R' is H or R⁴), and R⁴ is alkyl having 1–6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1–6 carbon atoms and the alkyl portion has 1–6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1–4 carbon atoms, such as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl; phthalidyl; benzyloxyalkyl having 8–10 carbon atoms, such as benzyloxymethyl, and (4-nitro) benzyloxymethyl.

In addition to the esters (and thio esters) listed above, amides are also embraced by the present invention, i.e., wherein X' is the —NR'-group. Representative of such amides are those wherein R' is selected from the group consisting of hydrogen and alkyl such as methyl and ethyl.

The most preferred —COX'R⁴ radicals of the present invention are those wherein (relative to Structure I above), X' is oxygen and R⁴ is hydrogen; loweralkyl having 1-4 carbon atoms; lower alkenyl such as 3-methylbutenyl, allyl, 2,2,2-trichloroethyl, 4-butenyl and the like; benzyl and substituted benzyl such as o-nitrobenzyl, p-nitrobenzyl; pivaloyloxymethyl, 3-phthalidyl; phenacyl, acetonyl; and triorganosilyl, such as trimethylsilyl.

Removal of the preferred protecting groups is categorized as follows:

a. for hydroxyl and amino functionalities bearing p-nitrobenzyloxycarbonyl protection or a carboxyl functionality possessing a p-nitrobenzyl moiety deprotection is accomplished by catalytic hydrogenation over a transition metal catalyst such as palladium supported on carbon, palladium hydroxide on carbon, or plantinum oxide, in an inert solvent or solvent mixtures, which maybe buffered in the usual way, such as tetrahydrofuran, dioxane, ethyl acetate, ethanol, and water, at a temperature of from 0° C. to ambient temperature, at a pressure of from 1 atmosphere to 5 atomospheres of hydrogen, for a period of from a few minutes to twelve hours;

b. for hydroxyl functions covered by a tbutyldimethylsilyl (TBDMS) group removal is accomplished according to the procedure of G. Just and T. J. Liak, *Can. J. Chem.*, 56, 211 (1978), which comprises treating the TBDMS ether derivative with N-tetrabutyl ammonium fluoride in the presence of acetic acid in an inert solvent such as tetrahydrofuran at a temperature of from −78° C. to ambient temperature for from a few minutes to 72 hours;

c. for carboxyl moieties possessing an allyl moiety and for hydroxyl and amino groups bearing an allyloxycarbonyl function deprotection is accomplished by treatment with a combination of triphenyl phosphine, tetrakistriphenylphosphine palladium (O), and 2-ethylhexanoic acid or its sodium or potassium salts in a suitable aprotic solvent such as ethylacetate, methylene chloride, tetrahydrofuran, or diethylether. Use of either sodium or potassium 2-ethylhexanoate provides the corresponding salt; whereas 2-ethylhexanoic acid provides the free carboxylic acid. The process for removing an allylic group from allylic esters, carbonates and carbamates is described in European Patent Application No. 13,633 (Schering Corp.) and in S. W. McCombie, et al., *Tetrahedron Letters*, 22, 3489 (1981).

Relative to the generic description of the compounds of the present invention, I:

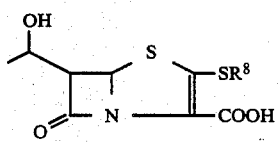

the following drawing depicts the most preferred configuration:

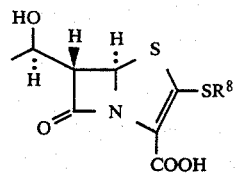

The compounds of the present invention (I) are valuable antibiotics active against various Gram-positive and Gram-negative bacteria and accordingly find utility in human and veterinary medicine. Representative pathogens which are sensitive to antibiotics I include: *Staphylococcus aureus, Escherichia coli, Klebsiella pneumoniae, Bacillus subtilis, Salmonella typhosa*, Psuedomonas and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example, in waterbased paints, and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, shuch as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semisolid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10-60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

In the foregoing word description, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents.

The following examples recite a precise scheme of synthesis. It is to be understood that the purpose of this recitation is to further illustrate the invention and not to impose any limitation. Temperature is in °C.

EXAMPLE 1

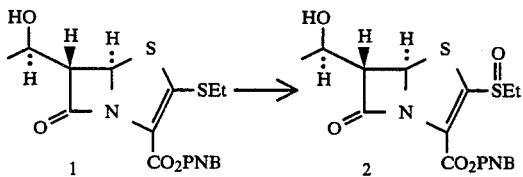

To a stirred solution of 300 mg (0.73 mmoles) of penem 1 in 5 ml of THF at −8° C. under an atmosphere of nitrogen was added dropwise a solution of 178.3 mg (0.88 mmoles) of 85% m-chloroperbenzoic acid in 5 ml $CH_2Cl_2$ over a period of 15 min. After the addition, the mixture was stirred further for 15 min. The mixture was partitioned between EtOAc/ice—$H_2O$/5% aq. sodium thiosulfate solution. The organic phase was separated and washed further with cold, dilute sodium bicarbonate solution, and then a saturated solution of sodium chloride. The organic phase was dried over $Na_2SO_4$, filtered, and evaporated. Purification by plate layer chromatography [1 development $CH_2Cl_2$—EtOAc (1:1)] afforded 51.8 mg (17%) of unreacted penem 1 and 115.6 mg (37%) of sulfoxide 2 as a mixture of diastereomers: IR($CH_2Cl_2$) 3400, 1795, 1701, 1524, 1320 and 1056 $cm^{-1}$; UV (dioxane) 348 and 261 nm; NMR ($CDCl_3$) $\delta$1.39 (d, J=6.5 Hz, $CH_3CH$), 1.43 (t, J=7.5 Hz, $CH_3CH_2$), 3.12 (m, $CH_3C\underline{H}_2$), 3.95 (dd, J=2 and 6.5 Hz, H6a), 3.98 (dd, J=2 and 6 Hz, H6b), 4.30 (m, $CH_3C\underline{H}$), 5.27 and 5.49 (two d's, J=14 Hz, $CH_2Ar$), 5.79 and 5.91 (two d's, J=2 Hz, H5a and H5b), 7.64, 7.68 and 8.30 (three d's, J=8.5 Hz, ArH). [Et=ethyl.]

EXAMPLE 2

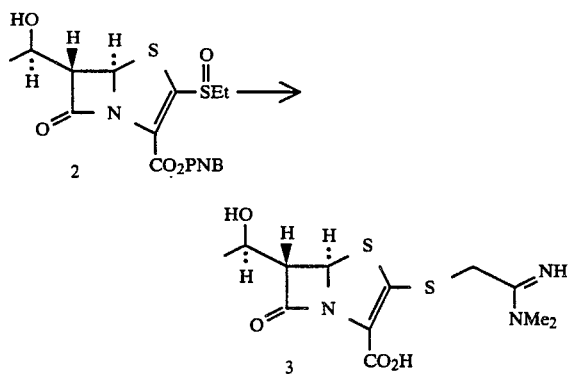

To a stirred solution of penem sulfoxide 2 (8.5 mg, 0.02 mmoles) in 1 ml THF and 0.25 ml of 0.1M pH 7.1 phosphate buffer at 0° C. was added in rapid succession a solution of 3.4 mg (0.022 mmoles) of N,N-dimethyl-2-mercaptoacetamidinium hydrochloride and 3.0 $\mu$l (0.022 mmoles) of diissopropylethylamine in 0.5 ml 0.1M pH 7.1 phosphate buffer and then 18 mg of 10% Pd/C. The mixture was hydrogenated at room temperature and 45 psi for 3.25 hours. The catalyst was removed by filtration and washed well with $H_2O$ and EtOAc. The filtrate was cooled in an ice—$H_2O$ bath and the aqueous phase was separated and washed with $Et_2O$. The aqueous phase was concentrated and purified by reverse phase plate layer chromatography [1 development 15% EtOH in $H_2O$] to give 1.65 mg (25.8%) of 3: $\lambda_{max}^{H2O}$ 319 nm; NMR ($D_2O$) 1.29, 3H(d, J=6.5 Hz); 3.16 3H(s); 3.31, 3H(s); 3.99, 1H(dd, J=1.5, 5.5 Hz); 4.01, 1H(d, J=16.0 Hz); 4.12, 1H(d, J=16 Hz): 4.25, 1H(m); 5.69, 1H(d, J=1.5 Hz). [Me=methyl.]

EXAMPLE 3

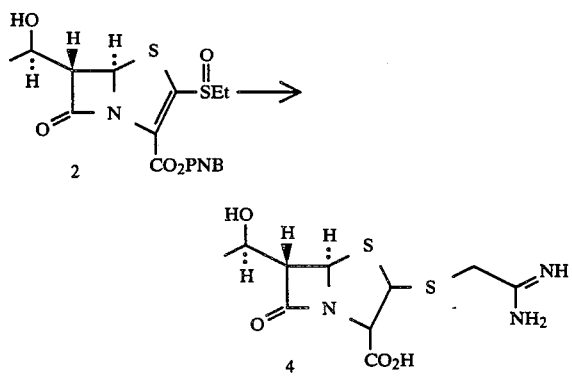

To a stirred solution of 7.6 mg (0.018 mmoles) of penem sulfoxide 2 in 1.0 ml THF and 0.25 ml of 0.1M pH 7.1 phosphate buffer at 0° C. under a nitrogen atmosphere was added in rapid succession a solution of 2.5 mg (0.02 mmoles) of 2-mercaptoacetamidinium hydrochloride and 3.4 μl (0.02 mmoles) of diisopropylethylamine in 0.5 ml of 0.1M pH 7.1 phosphate buffer and 10 mg of 10% Pd/C. The mixture was hydrogenated at room temperature and 50 psi for 4.0 hours. The catalyst was removed by filtration and washed with EtOAc and H$_2$O. The aqueous phase was separated, washed with Et$_2$O, concentrated in vacuo, and purified by reverse phase plate layer chromatography [1 development 5% EtOH in H$_2$O] to give the product 4: $\lambda_{max}^{H2O}$ 321.5 nm; NMR (D$_2$O)δ1.29, 3H(d, J=6.5 Hz); 3.98, 1H(dd, J=1.5, 5.5 Hz), 4.26, 1H(m), 5.72, 1H(d, J=1.5 Hz).

EXAMPLE 4

Following the procedures of the foregoing text and examples, the following "carbamimidoyl" embodiments of the present invention are obtained.

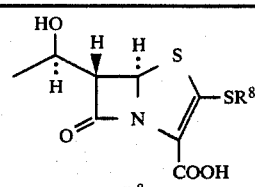

| Compound | R$^8$ |
|---|---|
| 5 | CH$_2$C(=NH)—NHCH$_3$ |
| 6 | CH$_2$C(=NH)—NHCH$_2$CH$_3$ |
| 7 | CH$_2$C(=NH)—NHCH(CH$_3$)$_2$ |
| 8 | CH$_2$C(=NH)—NHCH$_2$C$_6$H$_5$ |
| 9 | CH$_2$C(=NH)—NHCH$_2$-(2-pyridyl) |
| 10 | CH$_2$C(=NH)—NHC$_6$H$_5$ |
| 11 | CH(CH$_3$)C(=NH)—NH$_2$ |
| 12 | CH(CH$_3$)C(=NH)—NHCH$_3$ |
| 13 | CH(CH$_3$)C(=NH)—N(CH$_3$)$_2$ |
| 14 | CH(CH$_2$CH$_3$)C(=NH)—NH$_2$ |
| 15 | CH$_2$CH$_2$C(=NH)—NH$_2$ |
| 16 | CH$_2$CH$_2$C(=NH)—N(CH$_3$)$_2$ |
| 17 | CH$_2$CH$_2$CH$_2$C(=NH)—NH$_2$ |
| 18 | CH$_2$C(=NH)—NHCH$_2$-(4-pyridyl) |
| 19 | CH$_2$C(=NH)—N(CH$_3$)CH$_2$CH$_3$ |
| 20 | CH$_2$C(=NH)—N-morpholinyl |
| 21 | CH$_2$C(=NH)—N(CH$_2$CH$_3$)$_2$ |
| 22 | CH$_2$C(=NH)—N-pyrrolidinyl |
| 23 | CH$_2$C(=NH)—N-azetidinyl |
| 24 | CH$_2$C(=N—CN)—NH$_2$ |
| 25 | CH$_2$C(=N—SO$_2$NH$_2$)—NH$_2$ |
| 26 | CH$_2$-(2-imidazolinyl), NH |
| 27 | CH$_2$-(2-imidazolinyl), NCH$_3$ |
| 28 | CH$_2$-(N-methylbenzimidazoline) |
| 29 | CH$_2$C(=NCH$_3$)—N-pyrrolidinyl |

-continued

Structure (header for compounds 30–43):

carbapenem core with HO-CH(CH₃)- substituent, =CH-SR⁸ at C-2, COOH

| Compound | R⁸ |
|---|---|
| 30 | CH₂C(=NCH₂CH₃)—N(CH₃)₂ |
| 31 | CH₂C(=NH)—NHN(CH₃)₂ |
| 32 | CH₂C(=NH)—NHNH-(2-pyridyl) |
| 33 | 2-(methylamino)-1-pyrroline-5-yl (4,5-dihydro-2-methylamino-pyrrole, methyl at ring) |
| 34 | 2,3,5,6-tetrahydro-1H-pyrrolizine (bicyclic amidine) |
| 35 | 1-methyl-1,4,5,6-tetrahydropyrimidin-2-yl-CH₂ |
| 36 | (1-carboxymethyl-4,5-dihydroimidazol-2-yl)-CH₂ [CH₂-C with N=, N–CH₂CO₂H] |
| 37 | CH₂C(=NCH₃)—NHCH₃ |
| 38 | CH₂C(=NCH₃)—N(CH₃)₂ |
| 39 | CH₂CH₂C(=NH)—NHCH₃ |
| 40 | CH₂CH₂C(=NH)—NHCH₃ |
| 41 | CH₂CH₂C(=NH)—N(pyrrolidinyl) |
| 42 | CH₂-C(=N⁺(CH₃)₂)—N(CH₃)₂ |
| 43 | CH(OCH₃)—C(=NH)—NH₂ |

-continued

Structure (header for compounds 44–55): same carbapenem core

| Compound | R⁸ |
|---|---|
| 44 | CH₂=CH—C(=NH)—NH₂ |
| 45 | CH₂=CH—CH—C(=NH)—NH₂ |
| 46 | CH₂CH(OCH₃)—C(=NH)—NH₂ |
| 47 | CH₂—CH(OH)—C(=NH)—NH₂ |
| 48 | CH₂—C(=NOCH₃)—C(=NH)—NH₂ |
| 49 | CH₂—CH(N(CH₃)₂)—C(=NH)—NH₂ |
| 50 | CH₂—CH(N(CH₃)₃⁺Cl⁻)—C(=NH)—NH₂ |
| 51 | CH₂—CH(SCH₃)—C(=NH)—NH₂ |
| 52 | CH₂—C(=NH)—NHOCH₃ |
| 53 | CH₂—C(=NH)—N(CH₃)(OCH₃) |
| 54 | CH₂—C(CH₃)₂—C(=NH)—NH₂ |
| 55 | CH₂—C(=NH)—N(4-methylpiperazin-1-yl) |

-continued

| Compound | R⁸ |
|---|---|
| | (structure: HO-CH(CH₃)- with β-lactam, S, =C(SR⁸)COOH) |
| 56 | $-CH_2-\underset{\parallel}{\underset{NH}{C}}-NH-CH_2-$ (pyridyl) |
| 57 | $-CH_2-\underset{\parallel}{\underset{NH}{C}}-NH-$ (pyridyl) |
| 58 | $-CH_2-\underset{\parallel}{\underset{NH}{C}}-\underset{\underset{CH_3}{|}}{N}-N(CH_3)_2$ |
| 59 | $-CH_2-\underset{\parallel}{\underset{NH}{C}}-\underset{\underset{CH_3}{|}}{N}-NHCH_3$ |
| 60 | $-\underset{\underset{CH_3}{|}}{CH}-\underset{\parallel}{\underset{NH}{C}}-\underset{\underset{CH_3}{|}}{N}-N(CH_3)_2$ |
| 61 | $-CH_2-\underset{\parallel}{\underset{NH}{C}}-\underset{\underset{CH_3}{|}}{N}-O-CH_3$ |
| 62 | $-\underset{\underset{}{|}}{\underset{C_2H_5}{CH}}-\underset{\parallel}{\underset{NH}{C}}-NH_2$ |
| 63 | $-\underset{\underset{}{|}}{\underset{C_2H_5}{CH}}-\underset{\parallel}{\underset{NH}{C}}-N(CH_3)_2$ |
| 64 | $-\underset{\underset{CH_3}{|}}{CH}-CH_2-\underset{\parallel}{\underset{NH}{C}}-NH_2$ |
| 65 | $-CH_2-\underset{\underset{CH_3}{|}}{CH}-\underset{\parallel}{\underset{NH}{C}}-NH_2$ |

EXAMPLE 5

Preparation of Pharmaceutical Compositions

One such unit dosage form is prepared by mixing 120 mg of the compound of Example 2 (Compound 3) with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules, and, should it be necessary to make more than 145 mg of ingredients together, larger capsules such as compressed tablets and pills can be prepared. The following examples are illustrative of the preparation of pharmaceutical formulations:

| TABLET | PER TABLET |
|---|---|
| Compound 3 | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with the dicalcium phosphate, lactose and about half of the cornstarch. The mixture is then granulated with 15% cornstarch paste (16 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| Compound 3 | 500 mg. |
| Diluent: Sterile Water for Injection | 2 cc. |
| OPHTHALMIC SOLUTION | |
| Compound 3 | 100 mg. |
| Hydropropylmethyl Cellulose | 5 mg. |
| Sterile Water to | 1 ml. |
| OTIC SOLUTION | |
| Compound 3 | 100 mg. |
| Benzalkonium chloride | 0.1 mg. |
| Sterile Water to | 1 ml. |
| TOPICAL OINTMENT | |
| Compound 3 | 100 mg. |
| Polyethylene Glycol 4000 U.S.P. | 400 mg. |
| Polyethylene Glycol 400 U.S.P. | 1.0 gram |

What is claimed is:

1. A compound having the structural formula:

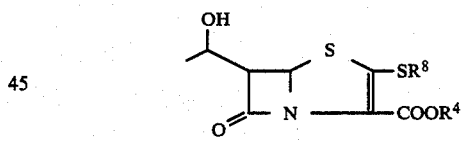

wherein R⁴ is H, a carboxylate salt cation, removable protecting group, or a pharmaceutically acceptable salt, ester or amide moiety; wherein: R⁸ is a carbamimidoyl selected from the group consisting of:

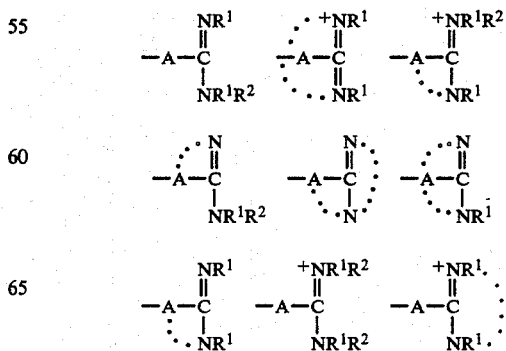

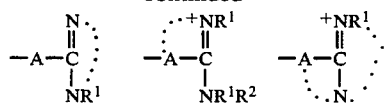

wherein: A is a single, direct bond, or A, the cyclic or acyclic connector, is selected from the group consisting of $C_{1-10}$ alkyl, which may be interrupted by a ring consisting of phenyl, cycloalkyl, heterocyclyl or heteroaryl wherein such cyclic interruptions comprise 3-6 ring atoms selected from C, O, S and N; cycloalkyl, heterocyclyl; heteroaryl; and phenyl; $R^1$ and $R^2$ are independently selected from: hydrogen, $N(R^a)_2$, $OR^a$, ($R^a$ is hydrogen or $C_{1-6}$alkyl), CN, $SO_2NH_2$ and the previously defined, but monovalent, values for the group A; and wherein the dotted lines indicate provision for cyclic structures formed by the joinder of the indicated nitrogen atom and the connector group A and by the joinder of the indicated nitrogen atoms.

2. A compound according to claim 1 wherein $-SR^8$ is selected from the group consisting of:

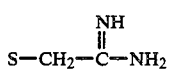 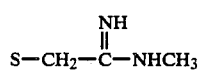

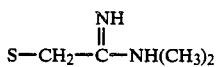 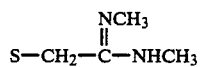

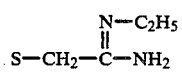 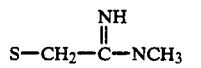

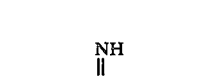 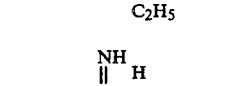

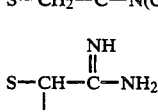 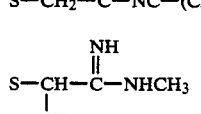

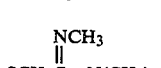 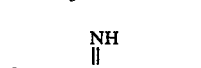

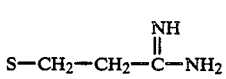 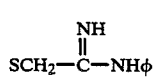

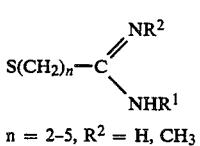

n = 2-5, $R^2$ = H, $CH_3$
$R^1$ = H, $CH_3$

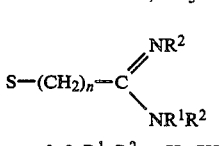

n = 2-5, $R^1$, $R^2$ = H, $CH_3$

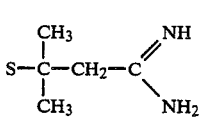

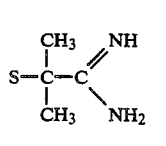

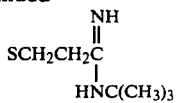

$R^1$ = H, $CH_3$

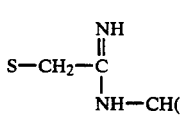

$R^1$ = H, $CH_3$
$R^2$ = H, $CH_3$

-continued
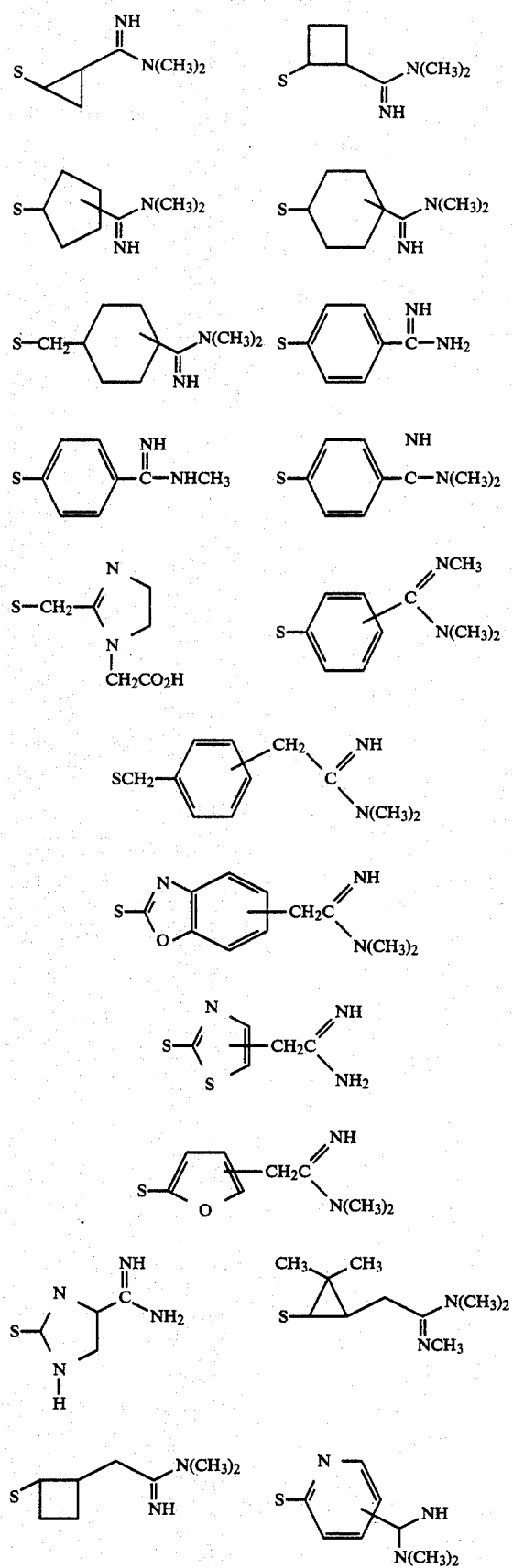
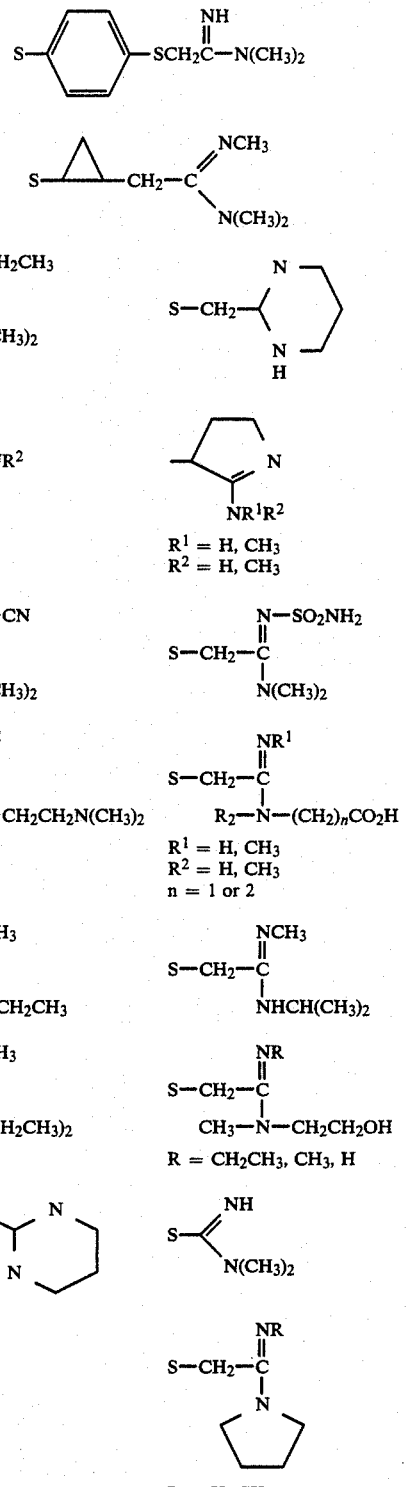
3. A method of treatment comprising administering an antibacterially effective amount of a compound according to claim 1.
4. An antibacterial composition comprising a therapeutically effective amount of a compound according to claim 1 and a pharmaceutically effective carrier therefor.
* * * * *